US008481570B2

United States Patent
Bender et al.

(10) Patent No.: US 8,481,570 B2
(45) Date of Patent: *Jul. 9, 2013

(54) 1-METHYLNICOTINAIDE DERIVATIVES AND FORMULATIONS OF TREATMENT OF LIPOPROTEIN ABNORMALITIES

(75) Inventors: Robert Bender, Ottawa (CA); Stefan Chlopicki, Krakow (PL); Jerzy Gebicki, Lodz (PL)

(73) Assignee: Cortria Corporation, Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/493,703

(22) Filed: Jun. 11, 2012

(65) Prior Publication Data

US 2012/0245115 A1   Sep. 27, 2012

Related U.S. Application Data

(60) Continuation of application No. 12/690,797, filed on Jan. 20, 2010, now Pat. No. 8,211,922, which is a division of application No. 11/484,892, filed on Jul. 11, 2006, now abandoned.

(60) Provisional application No. 60/698,292, filed on Jul. 11, 2005.

(51) Int. Cl.
*A01N 43/40* (2006.01)
*A01N 43/16* (2006.01)
*A61K 31/44* (2006.01)
*A61K 31/35* (2006.01)

(52) U.S. Cl.
USPC ............................ 514/355; 514/356; 514/460

(58) Field of Classification Search
USPC ........................................ 514/355, 356, 460
See application file for complete search history.

(56) References Cited

U.S. PATENT DOCUMENTS

| 5,260,305 | A | 11/1993 | Dennick |
| 6,090,830 | A | 7/2000 | Myers et al. |
| 6,129,930 | A | 10/2000 | Bova |
| 6,406,715 | B1 | 6/2002 | Cefali |
| 6,469,035 | B1 | 10/2002 | Cefali |
| 6,676,967 | B1 * | 1/2004 | Cefali et al. .................. 424/468 |
| 6,746,691 | B2 | 6/2004 | Cefali |
| 6,818,229 | B1 | 11/2004 | Cefali et al. |

(Continued)

FOREIGN PATENT DOCUMENTS

| DE | 840 698 C | 6/1952 |
| WO | WO 95/06470 A1 | 3/1995 |

(Continued)

OTHER PUBLICATIONS

Carlson, L.A., et al., "A Case of Massive Hypertriglyceridemia Corrected by Nicotinic Acid or Nicotinamide Therapy," *Atherosclerosis* 16:359-368, Elsevier Publishing Company, The Netherlands (1972).

(Continued)

*Primary Examiner* — Benjamin Packard
(74) *Attorney, Agent, or Firm* — Sterne, Kessler, Goldstein & Fox P.L.L.C.

(57) ABSTRACT

The present invention is directed to nicotinamide derivatives, and their use in treating lipoprotein abnormalities, alone or in combination with a statin.

19 Claims, 2 Drawing Sheets

U.S. PATENT DOCUMENTS

| | | |
|---|---|---|
| 7,011,848 B1 | 3/2006 | Bova |
| 2001/0014338 A1 | 8/2001 | Cefali |
| 2003/0157153 A1 | 8/2003 | Cefali |
| 2003/0158237 A1 | 8/2003 | Saragovi et al. |
| 2003/0161880 A1 | 8/2003 | Cefali |
| 2005/0255158 A1 | 11/2005 | Bova et al. |
| 2006/0263428 A1 | 11/2006 | Cefali |

FOREIGN PATENT DOCUMENTS

| | | |
|---|---|---|
| WO | WO 99/06046 A1 | 2/1999 |
| WO | WO 00/40559 A1 | 7/2000 |
| WO | WO 2005/067927 A2 | 7/2005 |
| WO | WO 2005/084323 A2 | 9/2005 |
| WO | WO 2006/052569 A1 | 5/2006 |

OTHER PUBLICATIONS

Filetti, S., et al., "Insulin Receptor Down-Regulation: Prevention at a Post-Receptor Site," *Endocrinology* 108(6):2409-2411, The Endocrine Society, United States (1981).

Fischer, L.J., et al., "Characteristics of Nicotinamide and $N^1$-Methylnicotinamide Protection from Alloxan Diabetes in Mice," *Toxicology and Applied Pharmacology* 70:148-155, Academic Press, Inc., United States (1983).

Fukushima, T., et al., "Possible role of 1-methylnicotinamide in the pathogenesis of Parkinson's disease," *Exp Toxic Pathol* 53:469-473, Urban & Fischer, Germany (2002).

Fukushima, T., et al., "Radical Formation Site of Cerebral Complex I and Parkinson's Disease," *Journal of Neuroscience Research* 42:385-390, Wiley-Liss, Inc., United States (1995).

Gebick, J., et al., "1-Methylnicotinamide: A Potent Anti-Inflammatory Agent of Vitamin Origin," *Pol. J. Pharmacol.* 55:109-112, Institute of Pharmacology, Polish Academy of Sciences, Poland (2003).

Lea, M.A., et al., "Effects of Nicotinamide and Structural Analogs on DNA Synthesis and Cellular Replication of Rat Hepatoma Cells," *Cancer Biochem Biophys.* 7:195-202, Gordon and Breach Science Publishers, Inc., England (1984).

Shibata, K., and Matsuo, H., "Correlation between niacin equivalent intake and urinary excretion of its metabolites, $N^1$-methyl-4-pyridone-3-carboxamide, in humans consuming a self-selected food," *Am J Clin Nutr* 50:114-119, American Society for Clinical Nutrition, United States (1989).

Taguchi, H., "Vitamins and apoptosis—Induction of apoptosis in human cancer cells by nicotinic acid-related compounds," *Nihon Rinsho* 57(10):2319-2324, Nihon Rinsho, Japan (1999) (Abstract only).

"Trigonella foenum-graecum," XP-002445860, GLOBinMED—Global Information Hub on Integrated Medicine, accessed at http://210.19.20.8/NHIContent/safetyDetail.aspx?id=SAF00013, accessed on Jul. 8, 2007, 8 pages.

\* cited by examiner

1-METHYLNICOTINAIDE DERIVATIVES AND FORMULATIONS OF TREATMENT OF LIPOPROTEIN ABNORMALITIES

RELATED APPLICATIONS

This application is a continuation application of U.S. application Ser. No. 12/690,797, filed on Jan. 20, 2010, which is a divisional application of U.S. application Ser. No. 11/484,892, filed on Jul. 11, 2006, which claims the benefit of Provisional Application No. 60/698,292, filed Jul. 11, 2005. The contents of the applications are incorporated by reference.

BACKGROUND OF THE INVENTION

It has been clear for several decades that high total cholesterol, high triglycerides, low high-density lipoprotein cholesterol, normal to elevated low-density lipoprotein cholesterol, or small low-density lipoprotein particles are related to a variety of diseases, conditions and disorders.

The evidence linking elevated serum cholesterol to coronary heart disease is overwhelming. (Badimon et al., Circulation, 86 Suppl. III, 1992, 86-94). Circulating cholesterol is carried by plasma lipoproteins, which are complex particles of lipid and protein that transport lipids in the blood. Low density lipoprotein (LDL) and high density lipoprotein (HDL) are the major cholesterol-carrier proteins. Id. LDL is believed to be responsible for the delivery of cholesterol from the liver, where it is synthesized or obtained from dietary sources, to extrahepatic tissues in the body. The term "reverse cholesterol transport" describes the transport of cholesterol from extrahepatic tissues to the liver, where it is catabolized and eliminated. It is believed that plasma HDL particles play a major role in the reverse transport process, acting as scavengers of tissue cholesterol. Id. HDL is also responsible for the removal non-cholesterol lipid, oxidized cholesterol and other oxidized products from the bloodstream.

Atherosclerosis, for example, is a slowly progressive disease characterized by the accumulation of cholesterol within the arterial wall. Compelling evidence supports the belief that lipids deposited in atherosclerotic lesions are derived primarily from plasma apolipoprotein B (apo B)-containing lipoproteins, which include chylomicrons, CLDL, IDL and LDL. See Badimon et al., 1992, Circulation 86:(Suppl. III)86-94. The apo B-containing lipoprotein, and in particular LDL, has popularly become known as the "bad" cholesterol. In contrast, HDL serum levels correlate inversely with coronary heart disease. Indeed, high serum levels of HDL is regarded as a negative risk factor. It is hypothesized that a high level of plasma HDL is not only protective against coronary artery disease, but may actually induce regression of atherosclerotic plaque. See Dansky and Fisher, 1999, Circulation 100: 1762-3. Thus, HDL has popularly become known as the "good" cholesterol.

Further, dyslipidemia is caused by various factors including, but not limited to, high total cholesterol, high triglycerides, low high-density lipoprotein cholesterol, normal to elevated low-density lipoprotein cholesterol, or small low-density lipoprotein particles.

Thus, there is a continued need to find new therapeutic agents to treat lipoprotein abnormalities. Accordingly, there is a great need to develop compounds and pharmaceutical compositions that will raise HDL levels, lower LDL levels, and/or lower triglyceride levels in a subject.

SUMMARY OF THE INVENTION

There remains a need for new treatments and therapies for lipoprotein abnormalities. There is also a need for compounds useful in the treatment or prevention or amelioration of one or more symptoms of lipoprotein abnormalities. Furthermore, there is a need for methods for raising HDL levels, lowering LDL levels and/or lowering triglyceride levels in a subject, using the compounds and pharmaceutical compositions provided herein.

Accordingly, in one aspect, the invention provides a compound of Formula I:

wherein R represents the group $NR^2R^3$ or the group $OR^4$; $R^1$ represents methyl; $R^2$ and $R^4$ each independently represent hydrogen or $C_{1-4}$ alkyl; $R^3$ represents hydrogen, $C_{1-4}$alkyl or $CH_2OH$; and $X^-$ is a physiologically suitable counter-anion. In one embodiment, R represents the group $NR^2R^3$. In another embodiment, $R^2$ represents methyl or hydrogen. In still another embodiment, $R^3$ represents $CH_2OH$ or hydrogen. In another embodiment, R represents the group $OR^4$, and $R^4$ represents $C_{1-4}$ alkyl. In yet another embodiment, $R^4$ represents propyl or ethyl. In another embodiment, the compound of Formula I is selected from a 1-methylnicotinamide salt or a 1-methyl-N'-hydroxymethylnicotinamide salt. In yet another embodiment, the compound of Formula I is selected from a 1-methylnicotinic acid ethyl ester salt or a 1-methylnicotinic acid propyl ester salt. In another embodiment, the compound of Formula I is selected from a 1-methylnicotinic acid salt. In another embodiment, the salt is a chloride, benzoate, salicylate, acetate, citrate or lactate. In another embodiment, the compound of Formula I is selected from 1-methylnicotinamide chloride, 1-methylnicotinamide citrate, 1-methylnicotinamide lactate, 1-methyl-N'-hydroxymethylnicotinamide chloride 1-methylnicotinic acid chloride, 1-methylnicotinic acid ethyl ester chloride or 1-methylnicotinic acid propyl ester chloride.

In another aspect, the invention is directed to a pharmaceutical composition comprising a statin and a compound of Formula I. In one embodiment, the statin is mevastatin, lovastatin, simvastatin, pravastatin, fluvastatin, pitavastatin, atorvastatin, cerivastatin, rosuvastatin, pentostatin or nystatin, or a pharmaceutically acceptable salt, solvate, clathrate, polymorph, prodrug, or pharmacologically active metabolite thereof.

In yet another aspect, the invention provides a method of treating a lipoprotein abnormality in a subject in need thereof by administering to the subject a pharmaceutical composition comprising a statin and a compound of Formula I. In another embodiment, the lipoprotein abnormality is a disease or disorder associated with the development and progress of atherosclerosis, hyperlipidaemias, angina pectoris or cardiac risk. In another embodiment, the disease or disorder associated with the development and progress of atherosclerosis is hypertension, dyslipidaemias, diabetes or obesity. In another embodiment, said treatment of atherosclerosis slows the progression of atherosclerotic plaques. In still another embodiment, said progression of atherosclerotic plaques is slowed in coronary arteries. In another embodiment, said progression of atherosclerotic plaques is slowed in carotid arteries. In yet another embodiment, said progression of atherosclerotic plaques is slowed in the peripheral arterial system. In another embodiment, said treatment of atherosclerosis causes the regression of atherosclerotic plaques. In another embodiment, said regression of atherosclerotic plaques occurs in coronary arteries. In another embodiment, the lipoprotein abnormality is associated with hypertension, cerebral vasospasm, coronary vasospasm, bronchial asthma, preterm labor, erectile dysfunction, glaucoma, vascular smooth muscle cell proliferation, myocardial hypertrophy, malignoma, ischemia/reperfusion-induced injury, endothelial dysfunction, Crohn's Disease and colitis, neurite outgrowth, Raynaud's Disease, angina, Alzheimer's disease or benign prostatic hyperplasia. In another embodiment, the lipoprotein abnormality is associated with erectile dysfunction, reperfusion/ischemia, or vasospasm. In another embodiment, the lipoprotein abnormality is associated with dementia or cancer. In another embodiment, the cancer is selected from the group consisting of prostate, skin, lung, colon, bladder, uterus and kidney cancer.

In yet another embodiment, the lipoprotein abnormality is associated with cardiovascular disease, peripheral vascular disease, dyslipidemia, dyslipoproteinemia, restenosis, a disorder of glucose metabolism, Alzheimer's Disease, Syndrome X, a peroxisome proliferator activated receptor-associated disorder, septicemia, a thrombotic disorder, obesity, pancreatitis, hypertension, renal disease, cancer, inflammation, inflammatory muscle diseases, such as polymyalgia rheumatica, polymyositis, and fibrositis, impotence, gastrointestinal disease, irritable bowel syndrome, inflammatory bowel disease, inflammatory disorders, impotence, arthritis, osteoporosis, soft tissue rheumatism, autoimmune disease, scleroderma, ankylosing spondylitis, gout, pseudogout, non-insulin dependent diabetes mellitus, septic shock, polycystic ovarian disease, hyperlipidemias, lipoprotein lipase deficiencies, lipoprotein abnormalities associated with diabetes, lipoprotein abnormalities associated with obesity, and lipoprotein abnormalities associated with Alzheimer's Disease.

In another embodiment, the statin and compound of Formula I are co-administered to the subject. In another embodiment, the statin and compound of Formula I administered sequentially to the subject. In another embodiment, the statin and compound of Formula I are administered orally, nasally, rectally, intravaginally, parenterally, buccally, sublingually or topically.

In another embodiment, the statin and a compound of Formula I are formulated using one or more pharmaceutically acceptable excipients chosen from starch, sugar, cellulose, diluent, granulating agent, lubricant, binder, disintegrating agent, wetting agent, emulsifier, coloring agent, release agent, coating agent, sweetening agent, flavoring agent, perfuming agent, preservative, antioxidant, plasticizer, gelling agent, thickener, hardener, setting agent, suspending agent, surfactant, humectant, carrier, stabilizer, or a combination thereof. In another embodiment, the statin and a compound of Formula I are each administered from one to five times per day. In another embodiment, the statin and a compound of Formula I are each administered one time per day. In yet another embodiment, the subject is a mammal. In another embodiment, the subject is a human. In another embodiment, the pharmaceutical composition further comprises a pharmaceutically acceptable carrier or excipient.

In another embodiment, the invention provides a pharmaceutical composition, together with one or more pharmaceutically acceptable carriers, diluents or excipients. In another embodiment, the invention provides pharmaceutical composition wherein the pharmaceutical composition is in tablet form. In yet another embodiment, the pharmaceutical composition is in capsule form. In another embodiment, the pharmaceutical composition is in controlled release or sustained release form.

In another embodiment, the invention provides a method of treating atherosclerosis in a subject in need thereof by administering to the subject a pharmaceutical composition comprising a statin and a compound of Formula I. In another embodiment, the invention provides a method of lowering LDL-cholesterol levels in a subject in need thereof by administering to the subject a pharmaceutical composition comprising a statin and a compound of Formula I. In still another embodiment, the invention provides a method of raising HDL-cholesterol levels in a subject in need thereof by administering to the subject a pharmaceutical composition comprising a statin and a compound of Formula I.

In another aspect, the invention provides a method of treating a lipoprotein abnormality in a subject in need thereof by administering to the subject a pharmaceutical composition comprising a statin and a compound of Formula I, wherein the compound of Formula I is administered first followed by administration of the statin. In yet another aspect, the invention provides a method of treating a lipoprotein abnormality in a subject in need thereof by administering to the subject a pharmaceutical composition comprising a statin and a compound of Formula I, wherein the statin is administered first followed by administration of the compound of Formula I. In still another aspect, the invention provides a method of treating a lipoprotein abnormality in a subject in need thereof by administering to the subject a pharmaceutical composition comprising a statin and a compound of Formula I, wherein the statin and the compound of Formula I are administered simultaneously. In a particular embodiment, the lipoprotein abnormality is atherosclerosis, a low HDL level, a high LDL level or high total cholesterol, or any combination thereof.

DETAILED DESCRIPTION OF THE INVENTION

It is well known that nicotinic acid (NAc) in high doses possesses important properties in the correction of lipoprotein profile (i.e. the treatment of lipoprotein abnormalities), mostly by reducing triglyceride (TG) and elevating HDL levels. The main disadvantage of nicotinic acid therapy is associated with its side effects. Very frequently, cutaneous vasolidation and flushing are observed.

Studies performed by the instant inventors have demonstrated that a pyridinium salt, namely, methylnicotinamide (MNA), is a molecule that can be used for the treatment of lipoprotein abnormalities. MNA is bound as a cationic molecule to Sepharose immobilized heparin (see e.g., International Application No. PCT/EP2005/050057, incorporated herein by reference). It was found that MNA releases PGI$_2$ and it is cytoprotective to various cell lines. In addition, MNA is chemically very stable, non-toxic and very well tolerated.

The statins are a family of compounds that are usually inhibitors of 3-hydroxy-3-methylglutaryl coenzyme A (HMG-CoA) reductase, the rate-limiting enzyme in cholesterol biosynthesis. As HMG-CoA reductase inhibitors, the statins are able to reduce plasma cholesterol levels in various mammalian species, including humans and are therefore effective in the treatment of hypercholesterolaemia.

The present invention is directed to nicotinamide derivatives, a pharmaceutical composition comprising a statin and a nicotinamide derivative, and their use in treating disorders, such as lipoprotein abnormalities. In particular, specific embodiments of the invention are described herein as exemplary embodiments and are not intended to be limiting.

Definitions

These and other embodiments of the invention will be described with reference to following definitions that, for convenience, are collected here.

The language "lipoprotein abnormality," as used herein, describes diseases and disorders that may be treated or prevented (or a symptom of such disease or disorder that may be reduced) by the compounds of the invention. In particular, a lipoprotein abnormality is caused by either high total cholesterol, high triglycerides, low high-density lipoprotein cholesterol, normal to elevated low-density lipoprotein cholesterol, or small low-density lipoprotein particles in a subject, or any combination thereof. These factors have been shown to play a role in a variety of diseases and disorders, including, but not limited to, a disorder associated with the development and progress of atherosclerosis (e.g., hypertension, dyslipidaemias, diabetes or obesity), hyperlipidaemias, angina pectoris or cardiac risk, cerebral vasospasm, coronary vasospasm, bronchial asthma, preterm labor, vascular smooth muscle cell proliferation, myocardial hypertrophy, malignoma, ischemia/reperfusion-induced injury, endothelial dysfunction, Crohn's Disease, colitis, neurite outgrowth, Raynaud's Disease, angina, Alzheimer's disease, benign prostatic hyperplasia, reperfusion/ischemia (e.g., stroke), vasospasm (e.g., cerebral vasospasm or coronary vasospasm), dementia and cancer (e.g., prostate, skin, lung, colon, bladder, uterus and kidney cancer).

Lipoprotein abnormalities also include cardiovascular disease; peripheral vascular disease, dyslipoproteinemia, restenosis, disorders of glucose metabolism, Syndrome X, a peroxisome proliferator activated receptor-associated disorder, septicemia, a thrombotic disorder, pancreatitis, renal disease, inflammation, inflammatory muscle diseases (e.g., polymyalgia rheumatica, polymyositis, or fibrositis), impotence, gastrointestinal disease, irritable bowel syndrome, inflammatory bowel disease, inflammatory disorders, asthma, vasculitis, ulcerative colitis, Kawasaki disease, Wegener's granulomatosis, multiple sclerosis, autoimmune chronic hepatitis, arthritis, rheumatoid arthritis, juvenile rheumatoid arthritis, osteoarthritis, osteoporosis, soft tissue rheumatism, tendonitis, bursitis, autoimmune disease, scleroderma, ankylosing spondylitis, gout, pseudogout, non-insulin dependent diabetes mellitus (NIDDM), septic shock, polycystic ovarian disease, hyperlipidemias, familial combined hyperlipidemia, lipoprotein lipase deficiencies, hypoalphalipoproteinemia, lipoprotein abnormalities associated with diabetes, lipoprotein abnormalities associated with obesity, and lipoprotein abnormalities associated with Alzheimer's Disease.

Lipoprotein abnormalities also include diseases and disorders associated with dysfunction of the vascular endothelium, oxidative stress, insufficient production of endothelial prostacyclin $PGI_2$, low HDL levels, and/or high triglyceride levels.

In a particular embodiment, the lipoprotein abnormality is an acute cardiovascular event associated with atherosclerosis, in particular sudden cardiac death, acute coronary syndrome (including unstable coronary artery disease, and myocardial infarct), the necessity of coronary angioplasty, coronary-aortal by-pass surgery (CABG), any type of surgery with extracorporeal circulation, ischemic stroke, or peripheral circulation revascularization.

In another particular embodiment, the lipoprotein abnormality is atherosclerosis in patients with chronic coronary disease, ischemic cerebrovascular episode or artherosclerosis of the extremities, including obliterans.

In another particular embodiment, the lipoprotein abnormality is a condition or disease selected from the group of risk factors for atherosclerosis, comprising the following: hypercholesterolemia, arterial hypertension, smoking, hyperhomocysteinaemia, insulin resistance, menopause, aging, mental stress, infections, inflammatory states, including periodontal diseases, allograft vasculopathy and nitrate tolerance.

In another particular embodiment, the lipoprotein abnormality is dyslipidemia, in particular hypercholesterolemia or hypertriglyceridemia.

In another particular embodiment, the lipoprotein abnormality is thrombosis that is not related directly with atherosclerosis, in particular thrombosis associated with implantation of metallic vascular prostheses (stents), by-pass surgery hemodialysis or venous disease.

In another particular embodiment, the lipoprotein abnormality is selected from the following group: chronic heart failure, pulmonary hypertension, diabetic complications, such as diabetic retinopathy and diabetic neuropathy, nephrotic syndrome, chronic renal failure, adults respiratory distress syndrome, cystic fibrosis, chronic obstructive pulmonary disease, erectile dysfunction, sleep apnea, systemic lupus erythematosus, sickle cell anemia, non-specific inflammatory bowel diseases, gastric or duodenal ulcers, glaucoma, chronic liver disease, primary amyloidosis, and neurodegenerative diseases.

In a particular embodiment, lipoprotein abnormalities can be treated by raising HDL levels in a subject, decreasing LDL levels in a subject, lowering triglycerides in a subject, and/or lowering total cholesterol in a subject by administering to the subject in need thereof the nicotinamide derivatives of the invention, alone or in combination with a statin.

The term "treatment" or "treating," as used herein, is defined as the application or administration of a therapeutic agent, i.e., a compound of the invention (alone or in combination with a statin), to a subject, or application or administration of a therapeutic agent to an isolated tissue or cell line from a subject (e.g., for diagnosis or ex vivo applications), who has a lipoprotein abnormality, a symptom of a lipoprotein abnormality or a predisposition toward a lipoprotein abnormality, with the purpose to cure, heal, alleviate, relieve, alter, remedy, ameliorate, improve or affect the lipoprotein abnormality, the symptoms of the lipoprotein abnormality or the lipoprotein abnormality. Such treatments may be specifically tailored or modified, based on knowledge obtained from the field of pharmacogenomics.

The term "subject" includes living organisms in which lipoprotein abnormalities can occur, or which are susceptible to lipoprotein abnormalities. The term "subject" includes animals (e.g., mammals, e.g., cats, dogs, horses, pigs, cows, goats, sheep, rodents, e.g., mice or rats, rabbits, squirrels, bears, primates (e.g., chimpanzees, monkeys, gorillas, and humans)), as well as chickens, ducks, geese, and transgenic species thereof; and cells, e.g., immortalized or nonimmortalized cells, derived therefrom.

Administration of the compositions of the present invention to a subject to be treated can be carried out using known procedures, at dosages and for periods of time effective to inhibit lipoprotein abnormalities in the subject. An effective amount of the therapeutic compound necessary to achieve a therapeutic effect may vary according to factors such as the state of the disease or disorder in the subject, the age, sex, and weight of the subject, and the ability of the therapeutic compound to inhibit the lipoprotein abnormalities in the subject. Dosage regimens can be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention (e.g., MNA) is between 1 and 500 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

In particular, the selected dosage level will depend upon a variety of factors including the activity of the particular compound of the present invention employed, the time of administration, the rate of excretion of the particular compound being employed, the duration of the treatment, other drugs, compounds or materials used in combination with the particular compound employed, the age, sex, weight, condition, general health and prior medical history of the patient being treated, and like factors well known in the medical arts.

A medical doctor, e.g., physician or veterinarian, having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

The regimen of administration can affect what constitutes an effective amount. The therapeutic formulations can be administered to the subject either prior to or after the onset of a lipoprotein abnormality. Further, several divided dosages, as well as staggered dosages, can be administered daily or sequentially, or the dose can be continuously infused, or can be a bolus injection. Further, the dosages of the therapeutic formulations can be proportionally increased or decreased as indicated by the exigencies of the therapeutic or prophylactic situation.

In particular embodiments, it is especially advantageous to formulate compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a lipoprotein abnormality in subjects.

Compounds of the Invention

The nicotinamide derivatives of the invention, which are also referred to herein as compounds of the invention, or simply MNA, can be synthesized using techniques well-known the one skilled in the art of organic synthesis. Such derivatives are also described in International Patent Application No. PCT/EP2005/050057 and EP Patent No. 1 147 086, both of which are incorporated herein by reference in their entirety.

In one aspect, the nicotinamide derivatives of the instant invention are represented by the Formula I:

(or pharmaceutically acceptable salts thereof) wherein R represents the group $NR^2R^3$ or the group $OR^4$; $R^1$ represents methyl; $R^2$ and $R^4$ each independently represent hydrogen or $C_{1-4}$ alkyl; $R^3$ represents hydrogen, $C_{1-4}$ alkyl or $CH_2OH$; and $X^-$ is a physiologically suitable counter-anion. In one embodiment, R represents the group $NR^2R^3$. In another embodiment, $R^2$ represents methyl or hydrogen. In another embodiment, $R^3$ represents $CH_2OH$ or hydrogen. In yet another embodiment, R represents the group $OR^4$, and $R^4$ represents $C_{1-4}$ alkyl. In another embodiment, $R^4$ represents propyl or ethyl.

In a preferred embodiment, the compound of Formula I is selected from a 1-methylnicotinamide salt or a 1-methyl-N'-hydroxymethylnicotinamide salt. In another preferred embodiment, the compound of Formula I is selected from a 1-methylnicotinic acid ethyl ester salt or a 1-methylnicotinic acid propyl ester salt. In another preferred embodiment, Formula I is selected from a 1-methylnicotinic acid salt. In another preferred embodiment, the salt of Formula I is a chloride, benzoate, salicylate, acetate, citrate or lactate.

In another preferred embodiment, the compound of Formula I is selected from 1-methylnicotinamide chloride, 1-methylnicotinamide citrate, 1-methylnicotinamide lactate, 1-methyl-N'-hydroxymethylnicotinamide chloride 1-methylnicotinic acid chloride, 1-methylnicotinic acid ethyl ester chloride or 1-methylnicotinic acid propyl ester chloride.

In a preferred embodiment, the nicotinamide derivatives of Formula I, alone or in combination with a statin, slow the progression of atherosclerotic plaques (e.g., progression of atherosclerotic plaques is slowed in coronary arteries, in carotid arteries, in the peripheral arterial system) or cause the regression of atherosclerotic plaques.

In a another preferred embodiment, the nicotinamide derivatives of the invention, alone or in combination with a statin, raise HDL levels in a subject, decrease LDL levels in a subject, lower triglycerides in a subject, and/or lower total cholesterol in a subject.

In one embodiment, the invention provides a method of treating atherosclerosis in a subject in need thereof by administering to the subject a pharmaceutical composition comprising atorvastatin and a 1-methylnicotinic acid salt.

In another embodiment, the invention provides a method of treating atherosclerosis in a subject in need thereof by administering to the subject a pharmaceutical composition comprising fluvastatin and a 1-methylnicotinic acid salt.

In another embodiment, the invention provides a method of treating atherosclerosis in a subject in need thereof by administering to the subject a pharmaceutical composition comprising lovastatin and a 1-methylnicotinic acid salt.

In another embodiment, the invention provides a method of treating atherosclerosis in a subject in need thereof by administering to the subject a pharmaceutical composition comprising pitavastatin and a 1-methylnicotinic acid salt.

In another embodiment, the invention provides a method of treating atherosclerosis in a subject in need thereof by administering to the subject a pharmaceutical composition comprising pravastatin and a 1-methylnicotinic acid salt.

In another embodiment, the invention provides a method of treating atherosclerosis in a subject in need thereof by administering to the subject a pharmaceutical composition comprising rosuvastatin and a 1-methylnicotinic acid salt.

In another embodiment, the invention provides a method of treating atherosclerosis in a subject in need thereof by administering to the subject a pharmaceutical composition comprising simvastatin and a 1-methylnicotinic acid salt.

In one embodiment, the invention provides a method of lowering LDL-cholesterol levels in a subject in need thereof by administering to the subject a pharmaceutical composition comprising atorvastatin and a 1-methylnicotinic acid salt.

In another embodiment, the invention provides a method of lowering LDL-cholesterol levels in a subject in need thereof by administering to the subject a pharmaceutical composition comprising fluvastatin and a 1-methylnicotinic acid salt.

In another embodiment, the invention provides a method of lowering LDL-cholesterol levels in a subject in need thereof by administering to the subject a pharmaceutical composition comprising lovastatin and a 1-methylnicotinic acid salt.

In another embodiment, the invention provides a method of lowering LDL-cholesterol levels in a subject in need thereof by administering to the subject a pharmaceutical composition comprising pitavastatin and a 1-methylnicotinic acid salt.

In another embodiment, the invention provides a method of lowering LDL-cholesterol levels in a subject in need thereof by administering to the subject a pharmaceutical composition comprising pravastatin and a 1-methylnicotinic acid salt.

In another embodiment, the invention provides a method of lowering LDL-cholesterol levels in a subject in need thereof by administering to the subject a pharmaceutical composition comprising rosuvastatin and a 1-methylnicotinic acid salt.

In another embodiment, the invention provides a method of lowering LDL-cholesterol levels in a subject in need thereof by administering to the subject a pharmaceutical composition comprising simvastatin and a 1-methylnicotinic acid salt.

In one embodiment, the invention provides a method of raising HDL-cholesterol levels in a subject in need thereof by administering to the subject a pharmaceutical composition comprising atorvastatin and a 1-methylnicotinic acid salt.

In another embodiment, the invention provides a method of raising HDL-cholesterol levels in a subject in need thereof by administering to the subject a pharmaceutical composition comprising fluvastatin and a 1-methylnicotinic acid salt.

In another embodiment, the invention provides a method of raising HDL-cholesterol levels in a subject in need thereof by administering to the subject a pharmaceutical composition comprising lovastatin and a 1-methylnicotinic acid salt.

In another embodiment, the invention provides a method of raising HDL-cholesterol levels in a subject in need thereof by administering to the subject a pharmaceutical composition comprising pitavastatin and a 1-methylnicotinic acid salt.

In another embodiment, the invention provides a method of raising HDL-cholesterol levels in a subject in need thereof by administering to the subject a pharmaceutical composition comprising pravastatin and a 1-methylnicotinic acid salt.

In another embodiment, the invention provides a method of raising HDL-cholesterol levels in a subject in need thereof by administering to the subject a pharmaceutical composition comprising rosuvastatin and a 1-methylnicotinic acid salt.

In another embodiment, the invention provides a method of raising HDL-cholesterol levels in a subject in need thereof by administering to the subject a pharmaceutical composition comprising simvastatin and a 1-methylnicotinic acid salt.

Without being bound by theory, it is believed that the compounds of the invention are effective in treating lipoprotein abnormalities for the following reasons: on the surface of the vascular endothelium, polyanionic molecules, such as glycosaminoglycans, are present and it would be expected that the molecules able to manifest some endothelial potential should be bound to vascular endothelium. The nicotinamide compounds of Formula I, which are positively charged, bind to the negatively charged glycosaminoglycans present on the vascular endothelium surface due to electrostatic interactions. This binding can result in manifestation of various endothelial effects, some of which can be positive from pharmacologic view point, for example release of NO and/or prostacyclin. Further, this activity can result in the treatment or prevention of lipoprotein abnormalities (which can be caused by, e.g., high total cholesterol, high triglycerides, low high-density lipoprotein cholesterol, normal to elevated low-density lipoprotein cholesterol, or small low-density lipoprotein particles in the subject).

As used herein, the language "pharmaceutically acceptable salt" refers to a salt of the administered compounds prepared from pharmaceutically acceptable non-toxic acids including inorganic acids, organic acids, solvates, hydrates, or clathrates thereof. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. In a particular embodiment, the compound of the invention is in the chloride form of 1-methylnicotinamide.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term "alkyl" also includes alkenyl groups and alkynyl groups. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl. Moreover, the term $C_{3-6}$-cycloalkyl includes, but is not limited to, cyclopropyl, cyclopentyl, and cyclohexyl. As discussed below, these alkyl groups, as well as cycloalkyl groups, may be further substituted.

The term alkyl further includes alkyl groups which can further include oxygen, nitrogen, sulfur or phosphorous atoms replacing one or more carbons of the hydrocarbon backbone. In an embodiment, a straight chain or branched chain alkyl has 10 or fewer carbon atoms in its backbone (e.g., $C_1$-$C_{10}$ for straight chain, $C_3$-$C_{10}$ for branched chain), and more preferably 6 or fewer carbons. Likewise, preferred cycloalkyls have from 4-7 carbon atoms in their ring structure, and more preferably have 5 or 6 carbons in the ring structure.

Moreover, alkyl (e.g., methyl, ethyl, propyl, butyl, pentyl, hexyl, etc.) include both "unsubstituted alkyl" and "substituted alkyl", the latter of which refers to alkyl moieties having substituents replacing a hydrogen on one or more carbons of the hydrocarbon backbone, which allow the molecule to perform its intended function.

The term "substituted" is intended to describe moieties having substituents replacing a hydrogen on one or more atoms, e.g. C, O or N, of a molecule. Such substituents can include, for example, oxo, alkyl, alkoxy, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, morpholino, phenol, benzyl, phenyl, piperizine, cyclopentane, cyclohexane, pyridine, 5H-tetrazole, triazole, piperidine, or an aromatic or heteroaromatic moiety, and any combination thereof.

Further examples of substituents of the invention, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy); aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., —$NH_2$), $(CR'R'')_{0-3}CN$ (e.g., —CN), —$NO_2$, halogen (e.g., —F, —Cl, —Br, or —I), $(CR'R'')_{0-3}C$(halogen)$_3$ (e.g., —$CF_3$), $(CR'R'')_{0-3}CH$(halogen)$_2$, $(CR'R'')_{0-3}CH_2$(halogen), $(CR'R'')_{0-3}CONR'R''$, $(CR'R'')_{0-3}$(CNH)NR'R'', $(CR'R'')_{0-3}S(\text{—O})_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., —$SO_3H$, —$OSO_3H$), $(CR'R'')_{0-3}(CR'R'')_{0-3}H$ (e.g., —$CH_2OCH_3$ and —$OCH_3$), $(CR'R'')_{0-3}S(CR'R'')_{0-3}H$ (e.g., —SH and —$SCH_3$), $(CR'R'')_{0-3}OH$ (e.g., —OH), $(CR'R'')_{0-3}COR'$, $(CR'R'')_{0-3}$ (substituted or unsubstituted phenyl), $(CR'R'')_{0-3}(C_3$-$C_8$ cycloalkyl), $(CR'R'')_{0-3}CO_2R'$ (e.g., —$CO_2H$), or $(CR'R'')_{0-3}OR'$ group, or the side chain of any naturally occurring amino acid; wherein R' and R'' are each independently hydrogen, a $C_1$-$C_5$ alkyl, $C_2$-$C_5$ alkenyl, $C_2$-$C_5$ alkynyl, or aryl group. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, oxime, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety, and any combination thereof. In certain embodiments, a carbonyl moiety (C—O) may be further derivatized with an oxime moiety, e.g., an aldehyde moiety may be derivatized as its oxime (—C=N—OH) analog. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (i.e., benzyl)).

The term "alkenyl" includes unsaturated aliphatic groups analogous in length and possible substitution to the alkyls described above, but which contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Combination Therapies

The nicotinamide derivatives of the present invention are intended to be useful, e.g., in the methods of present invention, in combination with one or more additional compounds useful for treating lipoprotein abnormalities. These additional compounds may comprise compounds of the present invention or compounds, e.g., commercially available compounds, known to treat, prevent, or reduce the symptoms of a lipoprotein abnormality.

In particular, the nicotinamide derivatives of Formula I can co-administered with statins. The term "statin," where used in the specification and the appendant claims, is synonymous with the terms "3-hydroxy-3-methylglutary-1-Coenzyme A reductase inhibitor" and "HMG-CoA reductase inhibitor." These three terms are used interchangeably in the art. As the synonyms suggest, statins are inhibitors of 3-hydroxy-3-methylglutaryl Coenzyme A reductase and, as such, are effective in lowering the level of blood plasma cholesterol. Statins and pharmaceutically acceptable salts thereof are particularly useful in lowering low-density lipoprotein cholesterol levels in mammals, and particularly in humans.

In accordance with an aspect of the present invention there is provided a method of achieving a therapeutic effect for treating a patient suffering from a lipoprotein abnormality comprising administering a therapeutically effective amount of a pharmaceutical combination comprising as active ingredients I a nicotinamide of Formula I, or an acceptable salt thereof; (ii) (b) a statin or a pharmaceutically acceptable salt thereof to the patient. In another embodiment of this aspect of the present invention the therapeutic effect achieved is synergistic, in that, the therapeutic effect is greater than the sum of the therapeutic effect achieved by the administration of the active ingredients separately.

Statins suitable for use in the compositions and methods of the invention are also disclosed in U.S. Pat. Nos. 4,681,893; 5,273,995; 5,356,896; 5,354,772; 5,686,104; 5,969,156; and 6,126,971, each of which is incorporated herein in its entirety by reference. As some statins may exist in an inactive form, such as a lactone (e.g., simvastatin), the invention encompasses using the active form (e.g., b-hydroxy acid form) of them. See Physicians Desk Reference, 54.sup.th Ed. (2000) pp. 1917-1920.

Statins include mevastatin, lovastatin, simvastatin, pravastatin, fluvastatin, pitavastatin, atorvastatin, cerivastatin, rosuvastatin, pentostatin or nystatin, or a pharmaceutically acceptable salt, solvate, clathrate, polymorph, prodrug, or pharmacologically active metabolite thereof.

Preferred statins are those agents which have been marketed, most preferred are pravastatin (e.g., Pravachol™), fluvastatin, simvastatin (e.g., Zocor™), lovastatin (e.g., Mevacor™), atorvastatin, or pitavastatin or a pharmaceutically acceptable salt thereof.

The statins have also recently been reported to have potential utility in the treatment of dementia (The Lancet, 2000: 356; 1627-1631) and various cancers, e.g., prostate, skin, lung colon, bladder, uterus and kidney (Arch. Intern. Med. 2000, 160: 2363-2368). These disorders, which are treated herein as "lipoprotein abnormalities," can be treated by a nicotinamide derivative of Formula I, alone or in combination with a statin.

In some embodiments, a nicotinamide derivative of Formula I and a statin are included in a single composition, which is administered to a subject having a lipoprotein abnormality. In other embodiments, a nicotinamide derivative of Formula I and a statin are administered separately to such a subject. The first and at least one second compound may either be co-administered to a subject (i.e., at the same time) or be administered sequentially (i.e., one after the other).

A combination of compounds described herein can either result in synergistic increase in effectiveness against a lipoprotein abnormality, relative to effectiveness following administration of each compound when used alone, or such an increase can be additive. Compositions described herein typically include lower dosages of each compound in a composition, thereby avoiding adverse interactions between compounds and/or harmful side effects, such as ones which have been reported for similar compounds. Furthermore, normal amounts of each compound when given in combination could provide for greater efficacy in subjects who are either unresponsive or minimally responsive to each compound when used alone.

For example, statins have been associated with some side-effects, including myalgias, muscle cramps, myositis, myopathy, and other gastrointestinal problems. The administration of MNA in combination with a statin to a subject in need thereof may serve to counteract unwanted side-effects associated with statin use.

A synergistic effect can be calculated, for example, using suitable methods such as, for example, the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

Nicotinamide derivatives of the invention for administration can be in the range of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 gig to about 3,500 mg, about 5 μg to about 3,000 mg, about 10 μg to about 2,600 mg, about 20 μg to about 2,575 mg, about 30 g to about 2,550 mg, about 40 μg to about 2,500 mg, about 50 μg to about 2,475 mg, about 100 μg to about 2,450 mg, about 200 μg to about 2,425 mg, about 300 μg to about 2,000, about 400 μg to about 1,175 mg, about 500 μg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg. The nicotinamide derivatives of the invention may be administered in combination with a statin, wherein the statin is administered in a range described above.

In some embodiments, the dose of a nicotinamide derivative of the invention is between about 0.0001 mg and about 25 mg. In some embodiments, a dose of a nicotinamide derivative of the invention used in compositions described herein is less than about 100 mg, or less than about 80 mg, or less than about 60 mg, or less than about 50 mg, or less than about 30 mg, or less than about 20 mg, or less than about 10 mg, or less than about 5 mg, or less than about 2 mg, or less than about 0.5 mg. Similarly, in some embodiments, a dose of a second compound (i.e., a statin) as described herein is less than about 1000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg.

Formulations for Administration

In another embodiment, the present invention is directed to a packaged pharmaceutical composition comprising a container holding a therapeutically effective amount of a nicotinamide derivative of Formula I, alone and in combination with a statin; and instructions for using the compound to treat, prevent, or reduce one or more symptoms of one or more lipoprotein abnormalities in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions can contain information pertaining to the compound's ability to perform its intended function, e.g., treating, preventing, or reducing one or more lipoprotein abnormalities in a subject.

Another embodiment of the invention is a pharmaceutical composition comprising a therapeutically effective amount of a nicotinamide compound of Formula I and a pharmaceutically acceptable carrier.

The language "therapeutically effective amount" describes the amount of nicotinamide derivative of Formula I of the invention that is effective to treat one or more lipoprotein abnormalities in a subject.

The language "pharmaceutically acceptable carrier" includes a pharmaceutically acceptable material, composition or carrier, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. As used herein "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds can also be incorporated into the compositions.

The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin. In one embodiment, the pharmaceutically acceptable carrier is not DMSO alone.

The compounds for use in the invention can be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For example, for oral administration the compounds can be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets can be coated using suitable methods and coating materials such as OPADRY™ film coating systems available from Colorcon, West Point, Pa. (e.g., OPADRY™ OY Type, OY-C Type, Organic Enteric OY-P Type, Aqueous Enteric OY-A Type, OY-PM Type and OPADRY™ White, 32K18400). Liquid preparation for oral administration can be in the form of solutions, syrups or suspensions. The liquid preparations can be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Parenteral Administration

For parenteral administration, the compounds for use in the method of the invention can be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents can be used.

Transmucosal Administration

Transmucosal administration is carried out using any type of formulation or dosage unit suitable for application to mucosal tissue. For example, the selected active agent can be administered to the buccal mucosa in an adhesive tablet or patch, sublingually administered by placing a solid dosage form under the tongue, lingually administered by placing a solid dosage form on the tongue, administered nasally as droplets or a nasal spray, administered by inhalation of an aerosol formulation, a non-aerosol liquid formulation, or a dry powder, placed within or near the rectum ("transrectal" formulations), or administered to the urethra as a suppository, ointment, or the like.

Transurethral Administration

With regard to transurethral administration, the formulation can comprise a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials. A transurethral permeation enhancer can be included in the dosage from. Examples of suitable permeation enhancers include dimethylsulfoxide ("DMSO"), dimethyl formamide ("DMF"), N,N-dimethylacetamide ("DMA"), decylmethylsulfoxide ("C10 MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone™ from Nelson Research & Development Co., Irvine, Calif.), SEPA™ (available from Macrochem Co., Lexington, Mass.), surfactants as discussed above, including, for example, Tergitol™, Nonoxynol-9™ and TWEEN-80™, and lower alkanols such as ethanol.

Transrectal Administration

Transrectal dosage forms may include rectal suppositories, creams, ointments, and liquid formulations (enemas). The suppository, cream, ointment or liquid formulation for transrectal delivery comprises a therapeutically effective amount of the selected active agent and one or more conventional nontoxic carriers suitable for transrectal drug administration. The transrectal dosage forms of the present invention can be manufactured using conventional processes. The transrectal dosage unit can be fabricated to disintegrate rapidly or over a period of several hours. The time period for complete disintegration may be in the range of from about 10 minutes to about 6 hours, e.g., less than about 3 hours.

Vaginal or Perivaginal Administration

Vaginal or perivaginal dosage forms may include vaginal suppositories, creams, ointments, liquid formulations, pessaries, tampons, gels, pastes, foams or sprays. The suppository, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention can be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit can be fabricated to disintegrate rapidly or over a period of several hours. The time period for complete disintegration may be in the range of from about 10 minutes to about 6 hours, e.g., less than about 3 hours.

Intranasal or Inhalation Administration

The active agents may also be administered intranasally or by inhalation. Compositions for intranasal administration are generally liquid formulations for administration as a spray or in the form of drops, although powder formulations for intranasal administration, e.g., insufflations, nasal gels, creams, pastes or ointments or other suitable formulators can be used. For liquid formulations, the active agent can be formulated into a solution, e.g., water or isotonic saline, buffered or unbuffered, or as a suspension. In certain embodiments, such solutions or suspensions are isotonic relative to nasal secretions and of about the same pH, ranging e.g., from about pH 4.0 to about pH 7.4 or, from about pH 6.0 to about pH 7.0. Buffers should be physiologically compatible and include, for example, phosphate buffers. Furthermore, various devices are available in the art for the generation of drops, droplets and sprays, including droppers, squeeze bottles, and manually and electrically powered intranasal pump dispensers. Active agent containing intranasal carriers can also include nasal gels, creams, pastes or ointments with a viscosity of, e.g., from about 10 to about 6500 cps, or greater, depending on the desired sustained contact with the nasal mucosal surfaces. Such carrier viscous formulations may be based upon, for example, alkylcelluloses and/or other biocompatible carriers of high viscosity well known to the art (see e.g., Remington: The Science and Practice of Pharmacy, supra). Other ingredients, such as preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. Formulations for inhalation may be prepared as an aerosol, either a solution aerosol in which the active agent is solubilized in a carrier (e.g., propellant) or a dispersion aerosol in which the active agent is suspended or dispersed throughout a carrier and an optional solvent. Non-aerosol formulations for inhalation can take the form of a liquid, typically an aqueous suspension, although aqueous solutions may be used as well. In such a case, the carrier is typically a sodium chloride solution having a concentration such that the formulation is isotonic relative to normal body fluid. In addition to the carrier, the liquid formulations can contain water and/or excipients including an antimicrobial preservative (e.g., benzalkonium chloride, benzethonium chloride, chlorobutanol, phenylethyl alcohol, thimerosal and combinations thereof), a buffering agent (e.g., citric acid, potassium metaphosphate, potassium phosphate, sodium acetate, sodium citrate, and combinations thereof), a surfactant (e.g., polysorbate 80, sodium lauryl sulfate, sorbitan monopalmitate and combinations thereof), and/or a suspending agent (e.g., agar, bentonite, microcrystalline cellulose, sodium carboxymethylcellulose, hydroxypropyl methylcellulose, tragacanth, veegum and combinations thereof). Non-aerosol formulations for inhalation can also comprise dry powder formulations, particularly insufflations in which the powder has an average particle size of from about 0.1 µm to about 50 µm, e.g., from about 1 µm to about 25 µm.

Topical Formulations

Topical formulations can be in any form suitable for application to the body surface, and may comprise, for example, an ointment, cream, gel, lotion, solution, paste or the like, and/or may be prepared so as to contain liposomes, micelles, and/or microspheres. In certain embodiments, topical formulations herein are ointments, creams and gels.

Transdermal Administration

The compounds of the invention may also be administered through the skin or mucosal tissue using conventional transdermal drug delivery systems, wherein the agent is contained within a laminated structure (typically referred to as a transdermal "patch") that serves as a drug delivery device to be affixed to the skin. Transdermal drug delivery may involve passive diffusion or it may be facilitated using electrotransport, e.g., iontophoresis. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir which, in this case, may be either a polymeric matrix as described above, or it may be a liquid or hydrogel reservoir, or may take some other form.

Intrathecal Administration

One common system utilized for intrathecal administration is the APT Intrathecal treatment system available from Medtronic, Inc. APT Intrathecal uses a small pump that is surgically placed under the skin of the abdomen to deliver medication directly into the intrathecal space. The medication is delivered through a small tube called a catheter that is also surgically placed. The medication can then be administered directly to cells in the spinal cord involved in conveying sensory and motor signals associated with lower urinary tract disorders.

Intravesical Administration

The term intravesical administration is used herein in its conventional sense to mean delivery of a drug directly into the bladder. Suitable methods for intravesical administration can be found, for example, in U.S. Pat. Nos. 6,207,180 and 6,039,967.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. patent application Ser. No. 20030147952, U.S. patent application Ser. No. 20030104062, U.S. patent application Ser. No. 20030104053, U.S. patent application Ser. No. 20030044466, U.S. patent Application Ser. No. 20030039688, and U.S. patent application Ser. No. 20020051820. Additional dosage forms of this invention also include dosage forms as described in PCT Patent Application WO 03/35041, PCT Patent Application WO 03/35040, PCT Patent Application WO 03/35029, PCT Patent Application WO 03/35177, PCT Patent Application WO 03/35039, PCT Patent Application WO 02/96404, PCT Patent Application WO 02/32416, PCT Patent Application WO 01/97783, PCT Patent Application WO 01/56544, PCT Patent Application WO 01/32217, PCT Patent Application WO 98/55107, PCT Patent Application WO 98/11879, PCT Patent Application WO 97/47285, PCT Patent Application WO 93/18755, and PCT Patent Application WO 90/11757.

Controlled Release Formulations and Drug Delivery Systems

In certain embodiments, the formulations of the present invention can be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time can be as long as a month or more and should be a release which is longer that the same amount of agent administered in bolus form.

For sustained release, the compounds can be formulated with a suitable polymer or hydrophobic material which provides sustained release properties to the compounds. As such, the compounds for use the method of the invention can be administered in the form of microparticles for example, by injection or in the form of wafers or discs by implantation.

In a preferred embodiment of the invention, the nicotinamide compounds of Formula I, are administered to a subject, alone or in combination with a statin, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes after drug administration.

Dosing

The therapeutically effective amount or dose of a compound of the present invention will depend on the age, sex and weight of the patient, the current medical condition of the patient and the nature of the lipoprotein abnormalities being treated. The skilled artisan will be able to determine appropriate dosages depending on these and other factors.

A suitable dose of a compound of the present invention can be in the range of from about 0.001 mg to about 500 mg per day, such as from about 0.01 mg to about 100 mg, for example, from about 0.05 mg to about 50 mg, such as about 0.5 mg to about 25 mg per day. The dose can be administered in a single dosage or in multiple dosages, for example from 1 to 4 or more times per day. When multiple dosages are used, the amount of each dosage can be the same or different. For example a dose of 1 mg per day can be administered as two 0.5 mg doses, with about a 12 hour interval between doses.

It is understood that the amount of compound dosed per day can be administered every day, every other day, every 2 days, every 3 days, every 4 days, every 5 days, etc. For example, with every other day administration, a 5 mg per day dose can be initiated on Monday with a first subsequent 5 mg per day dose administered on Wednesday, a second subsequent 5 mg per day dose administered on Friday, etc.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Equivalents

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including reaction times, reaction size/volume, and experimental reagents, such as solvents, catalysts, pressures, atmospheric conditions, e.g., nitrogen atmosphere, and reducing/oxidizing agents, etc., with art-recognized alternatives and using no more than routine experimentation, are within the scope of the present application.

It is to be understood that wherever values and ranges are provided herein, e.g., in ages of subject populations, dosages, and blood levels, all values and ranges encompassed by these values and ranges, are meant to be encompassed within the scope of the present invention. Moreover, all values that fall within these ranges, as well as the upper or lower limits of a range of values, are also contemplated by the present application.

Incorporation by Reference

The contents of all references, issued patents, and published patent applications cited throughout this application are hereby expressly incorporated, by reference in their entireties. It should be understood that the use of any of the compounds described herein are within the scope of the present invention and are intended to be encompassed by the present invention and are expressly incorporated herein for all purposes.

EXEMPLIFICATION OF THE INVENTION

The invention is further illustrated by the following examples, which should not be construed as further limiting. For the experiments described herein, MNA refers to 1-methylnicotinamide chloride.

EXAMPLE 1

Anti-Atherogenic Effect of MNA after a Short-Term Use

The anti-atherogenic effect of MNA was investigated in 20 dyslipidemic and cardiologic patients. The enrollment criteria was: high level of TG (~250 mg/dl) and/or high level of total cholesterol (TC) ($\geq$200 mg/dl). The mean age of the patients was 57.5 (range 37-81 years). The enrolled patients were divided into two groups: dyslipidemic patients (4 patients) and dyslipidemic patients after acute coronary failure (myocardial infarction) (12 patients). The patients were treated with MNA for 2 weeks. The MNA was administered orally, three times a day, one capsule (30 mg MNA) after meal. The 16 patients have finished clinical examination.

The plasma levels of TC, TG, and HDL were measured at baseline and after 2 weeks of therapy. The level of LDL was measured in those cases where it was possible (due to high TG level).

It has been found that MNA reduced the TC (248 vs. 212 mg/dl) (−14.50%) and TG (409 vs. 216 mg/dl) (−47.2%) levels between the base-line and 2 weeks measurements. The substantial increase of the HDL was observed after 2 weeks therapy in a group of dyslipidemic patients. The increase of the HDL was not observed after 2 weeks therapy in a group of dyslipidemic patients after acute coronary failure (myocardial infarction). The significant reduction of TG/HDL ratio (9.60 vs. 5.25) was observed.

Results of this study are shown in Tables I and II. Patient nos. 1-4 were dyslipidemic. Patient nos. 5-16 were dyslipidemic patients after acute coronary failure (myocardial infarction).

TABLE I

| | | | TG | | | Total Cholesterol | | | LDL | | | HDL | | |
|---|---|---|---|---|---|---|---|---|---|---|---|---|---|---|
| Patient no. | Sex | Age | visit 1 [mg/dl] | visit 2 [mg/dl] | % | visit 1 [mg/dl] | visit 2 [mg/dl] | % | visit 1 [mg/dl] | visit 2 [mg/dl] | % | visit 1 [mg/dl] | visit 2 [mg/dl] | % |
| 1. | F | 53 | 206 | 200 | −2.91% | 301 | 280 | −6.98% | — | — | — | 51 | 67 | 31.37% |
| 2. | F | 64 | 381 | 213 | −44.09% | 183 | 188 | 2.73% | — | — | — | 33 | 45 | 36.36% |
| 3. | F | 81 | 590 | 160 | −72.88% | 293 | 243 | −17.06% | — | — | — | 42 | 72 | 71.43% |
| 4. | M | 48 | 269 | 222 | −17.47% | 243 | 231 | −4.94% | — | — | — | 49 | 42 | −14.29% |
| 5. | M | 66 | 323 | 243 | −24.77% | 237 | 251 | 5.91% | 137 | 162 | 18.25% | 36 | 40 | 11.11% |
| 6. | M | 53 | 488 | 239 | −51.02% | 274 | 260 | −5.11% | 138 | 171 | 23.91% | 38 | 41 | 7.89% |
| 7. | M | 37 | 387 | 175 | −54.78% | 192 | 208 | 8.33% | 55 | 114 | 107.27% | 60 | 59 | −1.67% |
| 8. | F | 54 | 409 | 209 | −48.90% | 253 | 155 | −38.74% | 138 | 82 | −40.58% | 34 | 31 | −8.82% |
| 9. | M | 53 | 478 | 208 | −56.49% | 232 | 130 | −43.97% | — | — | — | 55 | 41 | −25.45% |
| 10. | F | 76 | 350 | 181 | −48.29% | 245 | 203 | −17.14% | 120 | 121 | 0.83% | 55 | 45 | −18.18% |

TABLE I-continued

| Patient no. | Sex | Age | TG visit 1 [mg/dl] | TG visit 2 [mg/dl] | % | Total Cholesterol visit 1 [mg/dl] | Total Cholesterol visit 2 [mg/dl] | % | LDL visit 1 [mg/dl] | LDL visit 2 [mg/dl] | % | HDL visit 1 [mg/dl] | HDL visit 2 [mg/dl] | % |
|---|---|---|---|---|---|---|---|---|---|---|---|---|---|---|
| 11. | F | 78 | 301 | 185 | −38.54% | 257 | 194 | −24.51% | 146 | 111 | −23.97% | 50 | 46 | −8.00% |
| 12. | M | 42 | 305 | 207 | −32.13% | 231 | 159 | −31.17% | 126 | 81 | −35.71% | 44 | 37 | −15.91% |
| 13. | F | 56 | 461 | 339 | −26.46% | 264 | 253 | −4.17% | 130 | 149 | 14.62% | 42 | 36 | −14.29% |
| 14. | M | 50 | 547 | 240 | −56.12% | 310 | 271 | −12.58% | 100 | 178 | 78.00% | 41 | 45 | 9.76% |
| 15. | M | 48 | 305 | 259 | −15.08% | 221 | 229 | 3.62% | 131 | 148 | 12.98% | 29 | 29 | 0.00% |
| 16. | M | 61 | 752 | 181 | −75.93% | 242 | 146 | −39.67% | — | — | — | 49 | 38 | −22.45% |
| Mean Value | | 57.50 | 409.50 | 218.31 | −47.18% | 248.63 | 212.56 | −14.50% | 122.10 | 131.70 | 7.86% | 44.25 | 44.63 | 0.85% |
| Standard deviation | | 12.69 | 138.90 | 42.84 | | 35.15 | 47.15 | | 26.77 | 35.07 | | 8.93 | 11.89 | |

TABLE II

| Patient no. | Sex | Age | TG visit 1 [mg/dl] | TG visit 2 [mg/dl] | % | TG/HDL visit 1 [mg/dl] | TG/HDL visit 2 [mg/dl] | % | Uric Acid visit 1 [mg/dl] | Uric Acid visit 2 [mg/dl] | % | Glucose visit 1 [mg/dl] | Glucose visit 2 [mg/dl] | % |
|---|---|---|---|---|---|---|---|---|---|---|---|---|---|---|
| 1. | F | 53 | 206 | 200 | −2.91% | 4.04 | 2.99 | −26.10% | 5.26 | 5.31 | 0.95% | 82 | 89 | 8.54% |
| 2. | F | 64 | 381 | 213 | −44.09% | 11.55 | 4.73 | −59.00% | 5.4 | 5.26 | −2.59% | 143 | 128 | −10.49% |
| 3. | F | 81 | 590 | 160 | −72.88% | 14.05 | 2.22 | −84.18% | 5.9 | 5.8 | −1.69% | 98 | 97 | −1.02% |
| 4. | M | 48 | 269 | 222 | −17.47% | 5.49 | 5.29 | −3.72% | 6.01 | 7.33 | 21.96% | 106 | 111 | 4.72% |
| 5. | M | 66 | 323 | 243 | −24.77% | 8.97 | 6.08 | −32.29% | — | — | — | — | — | — |
| 6. | M | 53 | 488 | 239 | −51.02% | 12.84 | 5.83 | −54.61% | — | — | — | 167 | 152 | −8.98% |
| 7. | M | 37 | 387 | 175 | −54.78% | 6.45 | 2.97 | −54.01% | 8.6 | 7.2 | −16.28% | 79 | 81 | 2.53% |
| 8. | F | 54 | 409 | 209 | −48.90% | 12.03 | 6.74 | −43.95% | 4.3 | 4.4 | 2.33% | 83 | 89 | 7.23% |
| 9. | M | 53 | 478 | 208 | −56.49% | 8.69 | 5.07 | −41.63% | 14.5 | 8.9 | −38.62% | 121 | 90 | −25.62% |
| 10. | F | 76 | 350 | 181 | −48.29% | 6.36 | 4.02 | −36.79% | — | — | — | 96 | 101 | 5.21% |
| 11. | F | 78 | 301 | 185 | −38.54% | 6.02 | 4.02 | −33.19% | 7 | 9.6 | 37.14% | 110 | 129 | 17.27% |
| 12. | M | 42 | 305 | 207 | −32.13% | 6.93 | 5.59 | −19.29% | 6.2 | 6.6 | 6.45% | 119 | 96 | −19.33% |
| 13. | F | 56 | 461 | 339 | −26.46% | 10.98 | 9.42 | −14.21% | — | — | — | 82 | 82 | 0.00% |
| 14. | M | 50 | 547 | 240 | −56.12% | 13.34 | 5.33 | −60.02% | — | — | — | 88 | 96 | 9.09% |
| 15. | M | 48 | 305 | 259 | −15.08% | 10.52 | 8.93 | −15.08% | 5.7 | 5.7 | 0.00% | 95 | 113 | 18.95% |
| 16. | M | 61 | 752 | 181 | −75.93% | 15.35 | 4.76 | −68.96% | 6.9 | 5.3 | −23.19% | 85 | — | — |
| Mean Value | | 57.50 | 409.50 | 216.31 | −47.18% | 9.60 | 5.25 | −45.32% | | | | | | |
| Standard deviation | | 12.69 | 138.90 | 42.84 | | 3.46 | 1.96 | | | | | | | |

EXAMPLE 2

Anti-Atherogenic Effect of MNA after a Long Term Use

The anti-atherogenic effect of MNA was investigated in 2 dyslipidemic patients. The enrollment criteria was: high level of TG ($\geqq$250 mg/dl) and/or high level of TC ($\geqq$200 mg/dl). The patients were treated with MNA for 13 months. The MNA was administered orally, two times a day (50 mg MNA) after meal.

The plasma levels of TC, TG, and HDL were measured at baseline and during the therapy. The level of LDL was measured in those cases where it was possible (due to high TG level).

It has been found that MNA reduced significantly the TC and TG levels in these patients. An increase of HDL levels was observed after only a few months of therapy. Also, the reduction of TG/HDL ratio was observed. Results of this study are shown in Tables III-VI.

TABLE III

Patient 1, male, 58 years

| Time [months] | TG [mg/dl] | % | Total Cholesterol [mg/dl] | % |
|---|---|---|---|---|
| 0 | 964 | | 298 | |
| 1.5 | 218 | −77.39% | 153 | −48.66% |
| 6 | 255 | −73.55% | 177 | −40.60% |
| 12 | 315 | −67.32% | 229 | −23.15% |

TABLE IV

Patient 1, male, 58 years

| Time [months] | LDL [mg/dl] | % | HDL [mg/dl] | % | TG/HDL [mg/dl] | % |
|---|---|---|---|---|---|---|
| 0 | nm | | 30.7 | | 31.40 | |
| 1.5 | 81.4 | | 28.0 | −8.79% | 7.79 | −75.21% |
| 6 | 87.0 | | 38.6 | 25.73% | 6.61 | −78.96% |
| 12 | 118.0 | | 48.1 | 56.68% | 6.55 | −79.14% |

TABLE V

| | Patient 2, male, 57 years | | | |
|---|---|---|---|---|
| Time | TG | | Total Cholesterol | |
| [months] | [mg/dl] | % | [mg/dl] | % |
| 0 | 302 | | 365 | |
| 7 | 269 | −10.93% | 261 | −28.49% |
| 13 | 160 | −47.02% | 210 | −42.47% |

TABLE VI

| | Patient 2, male, 57 years | | | | | |
|---|---|---|---|---|---|---|
| Time | LDL | | HDL | | TG/HDL | |
| [months] | [mg/dl] | % | [mg/dl] | % | [mg/dl] | % |
| 0 | 273.0 | | 44.0 | | 6.86 | |
| 7 | 128.0 | −53.11% | 79.0 | 79.55% | 3.41 | −50.39% |
| 13 | 106.8 | −60.88% | 70.8 | 60.91% | 2.26 | −67.07% |

EXAMPLE 3

Anti-Atherogenic Effect of MNA after a Single Administration

The anti-atherogenic effect of MNA after single administration was also investigated in dyslipidemic patients. The patient was treated with 100 mg MNA. The plasma levels of TC, TG, and HDL were measured at baseline and after 1 and 3 hours. The level of LDL was not measured due to high TG level. It has been found that MNA reduced the TG (596 vs. 479 mg/dl) level between the base-line and after the administration measurements. The increase of the HDL (24.8 vs. 29.0 mg/dl) was observed after the administration. The significant reduction of TG/HDL ratio (24.0 vs. 16.5) was observed.

Results are shown in Table VII.

TABLE VII

| | male, 45 years | | | | | | | |
|---|---|---|---|---|---|---|---|---|
| Time | TG | | Total Cholesterol | | HDL | | TG/HDL | |
| [h] | [mg/dl] | % | [mg/dl] | % | [mg/dl] | % | [mg/dl] | % |
| 0 | 596 | | 186 | | 24.8 | | 24.03 | |
| 1 | 566 | −5.03% | 188 | 1.08% | 25.5 | 2.82% | 22.20 | −7.64% |
| 3 | 479 | −19.63% | 195 | 4.84% | 29.0 | 16.94% | 16.52 | −31.27% |

EXAMPLE 4

MNA Efficacy in the Rat Model of Hypertriglyceridemia

Rats fed a high-fructose diet develop hypertriglyceridemia, insulin resistance and a mild degree of hypertension abnormalities that mimic metabolic syndrome in humans (Boehm and Claudi-Boehm, Scand J Clin Lab Invest Suppl. 2005; 240:3-13). To demonstrate the effect of 1-methylnicotinamide in an animal model of hypertriglyceridemia, Wistar rats were randomly divided into three groups (see Bartus et al., Pharmacol Rep. 2005; 57 Suppl:127-37). One group was fed a control diet (basal AIN93) for 8 weeks, the second was fed an AIN93 diet supplemented with 60% fructose for 8 weeks, and the third was fed an AIN93 diet supplemented with 60% fructose that was additionally treated with 100 mg/kg of MNA for the last 4 weeks (after hypertriglicerydemia fully develops) and was given to drinking water. At the end of experiments rats were anaesthetized, and blood was withdrawn and anticoagulated. Triglyceride level in plasma was measured by standard spectrophotometric technique using commercially available kits. The experiment was then repeated with 10 mg/kg of MNA, which gave similar results.

Figure 1:
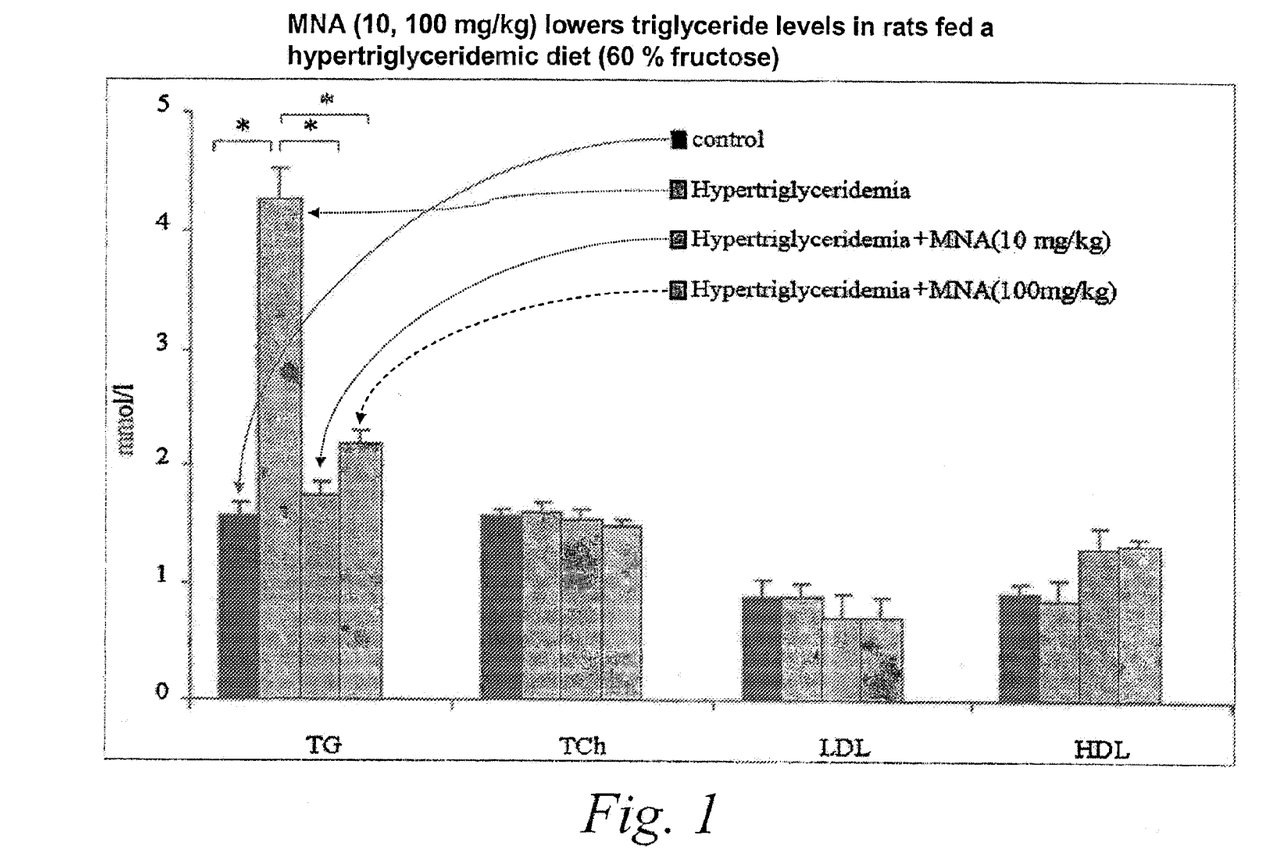
FIG. 1 demonstrates that MNA lowers triglyceride levels in rats fed a hypertriglyceridemic diet.

The results of this experiment, as shown in FIG. 1, demonstrate that 1-methylnicotinamide lowers triglyceride levels in rats fed a hypertriglyceridemic diet.

EXAMPLE 5

MNA Efficacy in the Mice Model of Atheroprotection

Gene targeted animal models of atherosclerosis, such as apoE and LDL receptor double knockout mice (Ishibashi et al., Proc Natl Acad Sci USA 1994; 91: 4431-4435; Bonthu et al., Arterioscler Thromb Vasc Biol 1997; 17: 2333-2340) represent a unique model of atherogenesis.

Methods

Animals

Female apoE/LDLR$^{-/-}$ mice on C57BL/6J background were used for experiments. The experiments were conducted according to the Guidelines for Animal Care and Treatment of the European Communities and were approved by the Local Animal Ethics Committee. apoE/LDLR$^{-/-}$ mice were fed with standard chow. MNA was given for 2 months (100 mg/kg, 4-6 months old apoE/LDLR$^{-/-}$ mice) and effects of MNA compared to placebo-treated mice. In each group of mice (control and MNA) n=5.

Quantitation of Atherosclerosis

Development of atherosclerosis was determined by cross-section (aortic roots), en-face (whole aorta) analysis and quantified semiautomatically, as described before (Jawien et al. Eur J Clin Invest; 2006; 36:141-6). Briefly, the heart and whole aorta were washed by phosphate buffered saline, then the heart and the whole aorta were removed. The heart and ascending aorta were embedded in OCT compound and snap-frozen. Ten micrometer-thick cryosections were cut and after fixation in 4% paraformaldehyde were stained with Meyer's hematoxylin and oil red-O and lesion area was measured semiautomatically in each slide using LSM Image Browser software.

Figure 2:
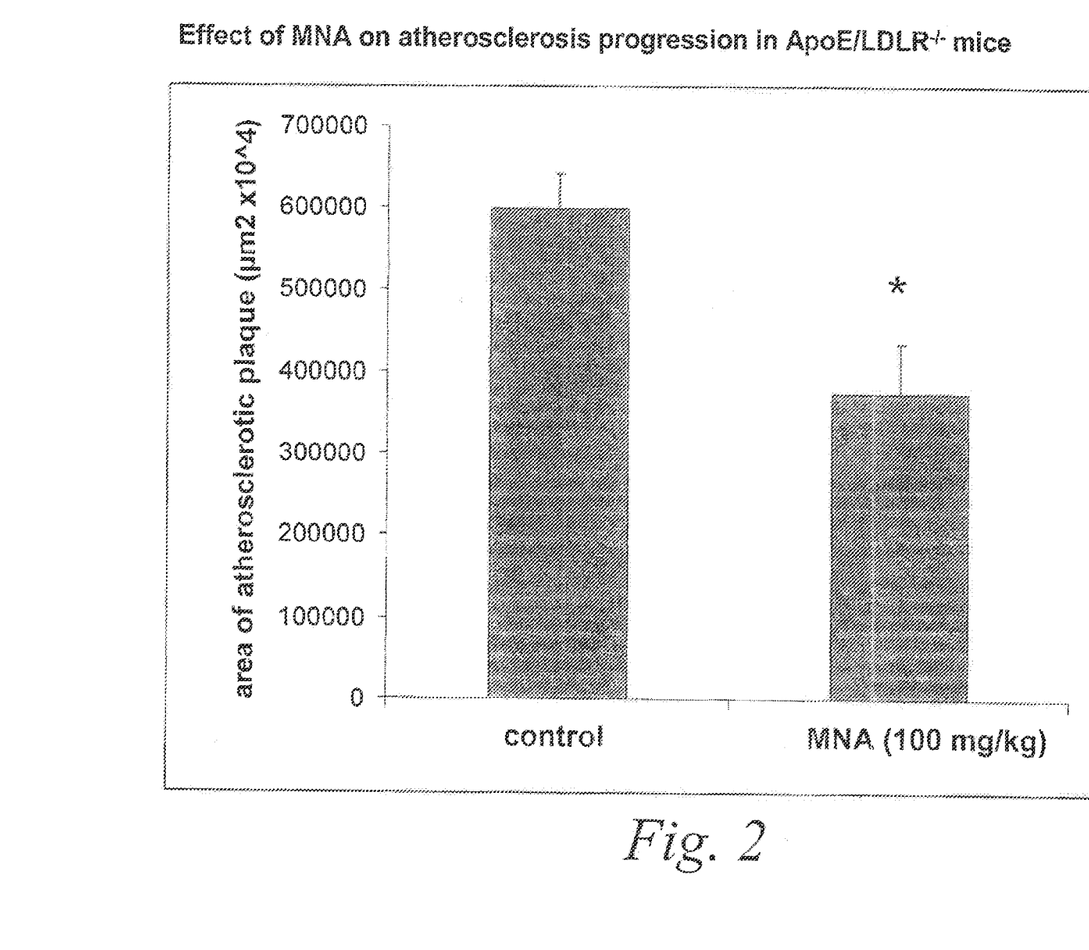
FIG. 2 demonstrates that MNA slows atherosclerosis progression in apoE/LDLR$^{-/-}$ mice.

The results of this experiment, as shown in FIG. 2, demonstrate that 1-methylnicotinamide slows atherosclerosis progression in apoE/LDLR$^{-/-}$ mice.

EXAMPLE 6

Safety of Co-Administration of MNA with Statins

A group of 10 patients (4 females and 6 males, ages 38-79) on permanent therapy with simvastatin (10-20 mg/day) were selected for the study. In addition to simvastatin each patient received MNA in daily dose of 90 mg/day for six weeks. The clinical chemistry parameters were monitored during three doctor's visits: two weeks before, just before and after six weeks of MNA administration. Based on patient examination no negative effects were observed as a result of MNA co-administration along with simvastatin. Also clinical chemistry parameters, in particular liver enzymes AST and ALT, creatinine, urea, glucose and homocysteine were not changed within the measurements accuracy.

This study demonstrates that MNA co-administration with statins does not result in any adverse synergistic effects.

EXAMPLE 7

Long Term MNA Use in Correction of the Lipoprotein Profile in Patients on Permanent Therapy with Statins A group of 8 patients (5 females and 3 males, ages 59-85) on permanent therapy with simvastatin or atorvastatin (10-20 mg/day) were selected for the study. MNA in a daily dose of 90-180 mg was co-administrated for a period of 3 to 42 months. The liporotein levels for each patient were monitored in every 1 to 3 months. In general, a long term co-administration of MNA resulted in the reduction of triglyceride (TG) level. The changes varied from patient to patient within a limit −5% to −42%. The appropriate changes in LDL were within −12% to +17% and in HDL within −6% to +37%. A particularly remarkable increase in HDL was observed in patients with a low starting HDL level (<40 mg/dl).

This example demonstrates that a long term co-administration of MNA with statins results in a decrease of TG and increase of HDL. Neither patients nor doctors involved with this study have declared any negative side effects from statin use, which could be associated with MNA co-administration.

The invention claimed is:

1. A method for increasing HDL-cholesterol levels in a human subject in need thereof, comprising administering orally to said subject a therapeutically effective amount of 1-methylnicotinamide or a pharmaceutically acceptable salt thereof and a therapeutically effective amount of a statin.

2. The method of claim 1 wherein said subject has low HDL-cholesterol levels before said administration.

3. The method of claim 1, wherein said 1-methylnicotinamide salt is selected from the group consisting of 1-methylnicotinamide chloride, 1-methylnicotinamide benzoate, 1-methylnicotinamide salicylate, 1-methylnicotinamide acetate, 1-methylnicotinamide citrate, and 1-methylnicotinamide lactate.

4. The method of claim 1, wherein said 1-methylnicotinamide or a pharmaceutically acceptable salt thereof and said statin are administered concurrently.

5. The method of claim 1, wherein said 1-methylnicotinamide or a pharmaceutically acceptable salt thereof and said statin are administered sequentially.

6. The method of claim 1, wherein said statin is selected from the group consisting of mevastatin, lovastatin, simvastatin, pravastatin, fluvastatin, pitavastatin, atorvastatin, cerivastatin, rosuvastatin, pentostatin, nystatin, a pharmaceutically acceptable salt thereof, and combinations thereof.

7. The method of claim 1, wherein said 1-methylnicotinamide or a pharmaceutically acceptable salt thereof and said statin are administered formulated in pharmaceutical compositions.

8. A method for decreasing triglyceride levels in a human subject in need thereof, comprising administering orally to said subject a therapeutically effective amount of 1-methylnicotinamide or a pharmaceutically acceptable salt thereof and a therapeutically effective amount of a statin.

9. The method of claim 8, wherein said 1-methylnicotinamide salt is selected from the group consisting of 1-methylnicotinamide chloride, 1-methylnicotinamide benzoate, 1-methylnicotinamide salicylate, 1-methylnicotinamide acetate, 1-methylnicotinamide citrate, and 1-methylnicotinamide lactate.

10. The method of claim 8, wherein said 1-methylnicotinamide or a pharmaceutically acceptable salt thereof and said statin are administered concurrently.

11. The method of claim 8, wherein said 1-methylnicotinamide or a pharmaceutically acceptable salt thereof and said statin are administered sequentially.

12. The method of claim 8, wherein said statin is selected from the group consisting of mevastatin, lovastatin, simvastatin, pravastatin, fluvastatin, pitavastatin, atorvastatin, cerivastatin, rosuvastatin, pentostatin, nystatin, a pharmaceutically acceptable salt thereof, and combinations thereof.

13. The method of claim 8, wherein said 1-methylnicotinamide or a pharmaceutically acceptable salt thereof and said statin are administered formulated in pharmaceutical compositions.

14. A method of treating atherosclerosis in a human subject in need thereof, comprising administering orally to said subject a therapeutically effective amount of a 1-methylnicotinamide or a pharmaceutically acceptable salt thereof and a therapeutically effective amount of a statin.

15. The method of claim 14, wherein said 1-methylnicotinamide salt is selected from the group consisting of 1-methylnicotinamide chloride, 1-methylnicotinamide benzoate, 1-methylnicotinamide salicylate, 1-methylnicotinamide acetate, 1-methylnicotinamide citrate, and 1-methylnicotinamide lactate.

16. The method of claim 14, wherein said 1-methylnicotinamide or a pharmaceutically acceptable salt thereof and said statin are administered concurrently.

17. The method of claim 14, wherein said 1-methylnicotinamide or a pharmaceutically acceptable salt thereof and said statin are administered sequentially.

18. The method of claim 14, wherein said statin is selected from the group consisting of mevastatin, lovastatin, simvastatin, pravastatin, fluvastatin, pitavastatin, atorvastatin, cerivastatin, rosuvastatin, pentostatin, nystatin, a pharmaceutically acceptable salt thereof, and combinations thereof.

19. The method of claim 14, wherein said 1-methylnicotinamide or a pharmaceutically acceptable salt thereof and said statin are administered formulated in pharmaceutical compositions.

* * * * *